(12) United States Patent
Andreou

(10) Patent No.: US 6,297,504 B1
(45) Date of Patent: Oct. 2, 2001

(54) METHOD AND APPARATUS FOR THE IMAGING OF GASES

(75) Inventor: Michael Paul Andreou, Horsham (GB)

(73) Assignee: Graham Thomas Consultants Limited, Fareham (GB)

(*) Notice: Subject to any disclaimer, the term of this patent is extended or adjusted under 35 U.S.C. 154(b) by 0 days.

(21) Appl. No.: 09/324,152

(22) Filed: Jun. 2, 1999

Related U.S. Application Data

(63) Continuation of application No. PCT/GB97/03311, filed on Dec. 1, 1997.

(30) Foreign Application Priority Data

Dec. 3, 1996 (GB) .................................................. 9625087

(51) Int. Cl.$^7$ .................................................. G01N 21/35
(52) U.S. Cl. .............. 250/330; 250/339.04; 250/339.14; 250/342
(58) Field of Search .................................... 250/330, 332, 250/338.5, 339.02, 339.04, 339.08, 339.13, 342; 356/451

(56) References Cited

U.S. PATENT DOCUMENTS 3,702,735  11/1972  Potter, Jr. .
5,539,518  7/1996  Bennett .

FOREIGN PATENT DOCUMENTS 0 153 139 A2  8/1985  (EP) .
0 235 404 A2  9/1987  (EP) .
0 287 929 A2  10/1988  (EP) .
WO 96/31766  10/1996  (WO) .

Primary Examiner—Georgia Epps
Assistant Examiner—Richard Hanig
(74) Attorney, Agent, or Firm—Wallenstein & Wagner, Ltd.

(57) ABSTRACT

A method for imaging a quantity of gas present in the atmosphere of a selected area. The method comprises the steps of directing background infra-red radiation from the selected area into an interferometer; imaging the infra-red radiation emerging from the interferometer onto at least one infra-red detector: obtaining a plurality of Fouriertransform infra-red spectra in the 8–14 micrometer spectral region, each spectrum coitesponding to infra-red radiation collected from a different portion of the selected area; and displaying in a suitable form an infra-red image, the infra-red image comprising the plurality of infra-red spectra, or quantities derived therefrom. The temperature of the quantity of gas or ambient temperature is measured, the temperature of the background is measured, and the difference between the two measured temperatures is used to derive gas column densities from the infra-red spectra.

15 Claims, 3 Drawing Sheets

METHOD AND APPARATUS FOR THE IMAGING OF GASES

This application is a continuation of International Application No. PCT/GB97/03311, filed Dec. 1, 1997, now pending, claiming priority from GB 9625087.3, filed Dec. 3, 1996 (which are hereby incorporated by reference).

BACKGROUND OF THE INVENTION

This invention relates to a method and apparatus for the imaging of gases, in particular to Fourier Transform Infrared (FTIR) imaging of gases.

Remote sensing—in particular, chemically selective remote sensing—of gas clouds, gas plumes and the like is a field of obvious environmental significance. Such gas clouds may be due, to, for instance, unintentional gas leakage or to the expulsion of gaseous effluents.

Infra-red vibrational spectroscopy in the 8–14 and 3–5 $\mu$m spectral regions is an analytical technique well suited to such investigations, since most molecules possess an unique infra-red spectrum, and the atmosphere is relatively transparent at these wavelengths. Thus it is perhaps surprising that there appears to be a dearth of literature concerning passive infra-red spectroscopic monitoring of gas clouds and the like. Passive monitoring—wherein absorption or emission of background infra-red radiation is detected—has obvious attractions due to its unobtrusiveness and simplicity is not necessary, for example, to provide an interrogating infra-red radiation source and to position a reflector for such a source, or to position a source at a distance from the detector.

FTIR spectroscopy is a technique of high sensitivity which is well suited to passive measurements. Of particular relevance to the present application is European Patent Application EP-A-0 287 929, which describes a device in which passive FTIR monitoring of gas clouds is combined with a video camera providing a visual image of the monitored area. However, since a single infra-red detector is employed in a standard interferometer arrangement, an infra-red spectrum is obtained which represents a single measurement over the entire field of view of the interferometer. Furthermore, the device does not produce truly quantitative concentration data, since temperature effects are not accounted for.

An improvement upon such passive FTIR systems would be a system capable of producing an IR image of a gas cloud. In this way, the cloud becomes "visible", since its size and location can be determined. The most straightforward practical implementation would be to employ some kind of array of IR detectors in conjunction with suitable imaging optics. In fact, the field of FTIR imaging appears to be a nascent one, a situation which is probably in large measure due to the fact that the computational requirements are quite severe: Fourier transforms must be performed upon a plurality of interferograms, corresponding to the plurality of detectors in the array, at a realistic duty cycle. It is only recently that suitably powerful data processing technologics have become routinely available.

To date, FTIR imaging appears to have been directed towards military applications such as the tracking of missile or jet vapour streams. It is more than arguable that the imaging of 'typical' gas clouds is a more exacting task, since jet omissions and the like are extremely hot typically, at temperatures of 500° C. or more, and therefore emit IR radiation strongly. Gas clouds produced for example, by accidental industrial gas leakage are likely to be at significantly lower temperatures, probably close to or at ambient temperature. Furthermore, such military directed imaging is not concerned with the derivation of quantitative data, i.e, gas column densities. Clearly, quantitative data is highly desirable in the context of gas cloud imaging: for example, such data indicates if a hazardous concentration threshold is being exceeded.

SUMMARY OF THE INVENTION

It is an object of the present invention to provide a passive FTIR gas cloud imaging system capable of generating quantitative gas concentration data.

It is a further object of the present invention to provide a composite gas cloud imaging device comprising a passive FTIR gas cloud imaging system combined with a camera system in which the results of the two interrogation techniques—an IR image and a visible image—are displayed simultaneously.

For the avoidance of doubt, the term "gas" is understood to encompass any species in the gas phase, including vapours.

According to a first aspect of the invention there is provided a method for imaging a quantity of gas present in the atmosphere of a selected area comprising the steps of:
  directing background IR radiation from the selected area into an interferometer;
  imaging the IR radiation emerging from the interferometer onto at least one IR detector;
  obtaining a plurality of FTIR spectra in the 8 to 14 $\mu$m spectral region, each spectrum corresponding to IR radiation collected from a different portion of the selected area; and
  displaying in a suitable form an IR image, said IR image comprising the plurality of IR spectra, or quantities derived therefrom;
  in which the temperature of the quantity of gas or ambient temperature is measured, the temperature of the background is measured, and the difference between the two measured temperatures is used to derive gas column densities from said IR spectra.

The method comprises a quantitative, passive FTIR imaging process in which the absorption or emission of constituents of a gas cloud, plume or the like are measured with respect to a background 'blackbody' IR radiation source.

The IR radiation emerging from the interferometer may be imaged onto an array of IR detectors, and each spectrum in the plurality of IR spectra may correspond to the transformed output of a detector in the array.

The background temperature may be measured from the intensity or the intensity distribution of the IR spectra.

The IR image may comprise quantities related to the intensity of an absorption or emission feature in the plurality of IR spectra. In this way, chemically selective intensity data may be displayed.

The difference between the two measured temperatures may be less than 20° C. In other words, the invention is applicable not only to the measurement of "hot" gases, in which the temperature difference is large, but also to "cool" gases, at near ambient temperature.

According to a second aspect of the invention there is provided a method for imaging a quantity of gas present in the atmosphere of a selected area comprising the steps of:
  directing background IR radiation from the selected area into an interferometer;
  imaging the IR radiation emerging from the interferometer onto at least one TR detector;

obtaining a plurality of FTIR spectra, each spectrum corresponding to IR radiation collected from a different portion of the selected area;

obtaining a visible image of an area which includes the selected area; and simultaneously displaying in a suitable form (i) an IR image, said IR image comprising the plurality of IR spectra, or quantities derived therefrom, and (ii) the visible image.

The IR radiation emerging from the interferometer may be imaged onto an array of IR detectors, each spectrum in the plurality of IR spectra corresponding to the transformed output of a detector in the array.

The IR image may comprise quantities related to the intensity of an absorption or emission feature in the plurality of IR spectra.

The display of the IR image man overlay the visible image in a portion of the visible image which substantially corresponds to the selected area.

The method according to the second aspect of the invention may also be in accordance with the first aspect of the invention.

According to the third aspect of the invention there is provided apparatus for imaging a quantity of gas present in the atmosphere of a selected area comprising:

an IR collection device capable of collecting IR radiation in the 8 to 14 $\mu$m spectral region;

an interferometer capable of analysing the collected IR radiation in the 8 to 14 $\mu$m spectral region comprising imaging means for imaging IR radiation emerging from the interferometer onto at least one IR detector, the interferometer producing a plurality of interferograms, each interferogram corresponding to a different portion of the selected area;

computing means for obtaining a plurality of IR spectra by performing Fourier transformations of the interferograms.

display means for displaying in a suitable form an IR image, said IR image comprising the plurality of IR spectra, or quantities derived therefrom;

means for measuring the temperature of the quantity of gas or ambient temperature;

means for measuring the temperature of the background;

in which the difference between the two measured temperatures is used by, the computing means to derive gas column densities from said IR spectra.

The interferometer may be a Michelson interferometer.

The apparatus may comprise an array of IR detectors in which IR radiation emerging from the interferometer is imaged onto said array and the computing means performs Fourier transformations on the interferograms resulting from each IR detector.

In preferred embodiments, the apparatus generates two dimensional IR images. In order to perform this function the apparatus may comprise a two dimensional array of IR detectors.

Alternatively, the array of IR detectors may comprise a linear array, and the IR collection device may be a scanning optical element, the scanning optical element being moveable so as to vary the portion of the selected area from which the IR radiation is imaged onto the linear array.

The one dimensional array may comprise at least eight IR detectors.

The display means may display an IR image comprising quantities related to the intensity of an absorption or emission feature in the plurality of IR spectra.

The imaging means may comprise an aspherical germanium lens combination.

The interferometer may comprise corner cube retroreflectors.

The detectors may comprise cooled mercury cadmium telluride detectors.

According to a fourth aspect of the invention there is provided apparatus for imagine a quantity of gas present in the atmosphere of a selected area comprising;

an IR collection device capable of collecting IR radiation;

an interferometer capable of analysing the collected IR radiation comprising imaging means for imaging IR radiation emerging from the interferometer onto at least one IR detector, the interferometer producing a plurality of interferograms, each interferogram corresponding to a different portion of the selected area;

computing means for obtaining a plurality of IR spectra by performing Fourier transformations of the plurality of interferograms;

a camera capable of generating a visible image of an area which includes the selected area; and display means for simultaneously displaying in a suitable form (i) an IR image comprising the plurality of IR spectra, or quantities derived therefrom, and (ii) the visible image.

The display means may display an IR image comprising quantities related to the intensity of an absorption or emission feature in the plurality of IR spectra.

The apparatus may comprise an array of IR detectors in which IR radiation emerging from the interferometer is imaged onto said array, and the computing means performs Fourier transformation on the interferograms resulting from each IR detector.

The display means may display the IR image in the portion of the visible image which substantially corresponds to the selected area.

The camera may be a CCD TV camera.

The apparatus according to the fourth aspect of the invention may also be in accordance with the third aspect of the invention.

BRIEF DESCRIPTION OF THE DRAWINGS

Apparatus and methods in accordance with the invention will now be described with reference to the accompanying drawings, in which.

DETAILED DESCRIPTION OF THE INVENTION

The present invention relates to a method for imaging a quantity of gas present in the atmosphere of a selected area, and to apparatus for performing this method. The quantity of gas may be a gas cloud, plume or the like, although the invention is not limited in this regard.

In one aspect, the method comprises the steps of:

directing background IR radiation from the selected area into a interferometer;

imaging the IR radiation emerging from the interferometer onto at least one IR detector;

obtaining a plurality of FTIR spectra in the 8 to 14 μm spectral region, each spectrum corresponding to IR radiation collected from a different portion of the selected area; and displaying in a suitable form an IR image, said IR image comprising the plurality of IR spectra, or quantities derived therefrom;

in which the temperature of the quantity of gas or ambient temperature is measured, the temperature of the background is measured, and the difference between the two measured temperatures is used to derive gas column densities from said IR spectra.

Thus, the method is a quantitative, passive FTIR imaging process. The manner in which the IR imaging is achieved is discussed more fully below. Before doing so, however, it is apposite to emphasise a number of points.

Firstly, the measurement technique is a passive one, in which IR spectra are obtained with respect to naturally occurring broad band background IR radiation. Such IR radiation emanates from (or is reflected from) a suitable backgrounds which may be, for example, the sky or an edifice, such as a wall. The type of spectrum produced—emission or absorption—depends upon the temperature of the quantity of gas relative to the temperature of the background: if the background is hotter than the gas, an absorption spectrum will result; if the background is colder than the gas, an emission spectrum will result.

Secondly, the technique is quantitative since column densities (dimensions of concentration×path length) can be derived from the intensities of the IR spectra. In order to obtain such quantitative data it is essential to correct the measured spectral intensities for the temperature difference between the gas and the background: as the magnitude of this temperature difference increases, the intensity of the IR absorption/emission spectrum of the gas increases. Furthermore, it has been recognised that temperature difference corrections of this type will only be successful if the spectra are obtained in the 8–14 μm spectral "window". Calculations have indicated that background 8–14 μm radiation is almost wholly due to blackbody thermal emission, whereas background radiation in the 3–5 μm spectral window has a significant component due to scattered solar radiation. Temperature difference corrections would be unable to account for this solar component if measurements in the 3–5 μm region were contemplated.

Figure 1:
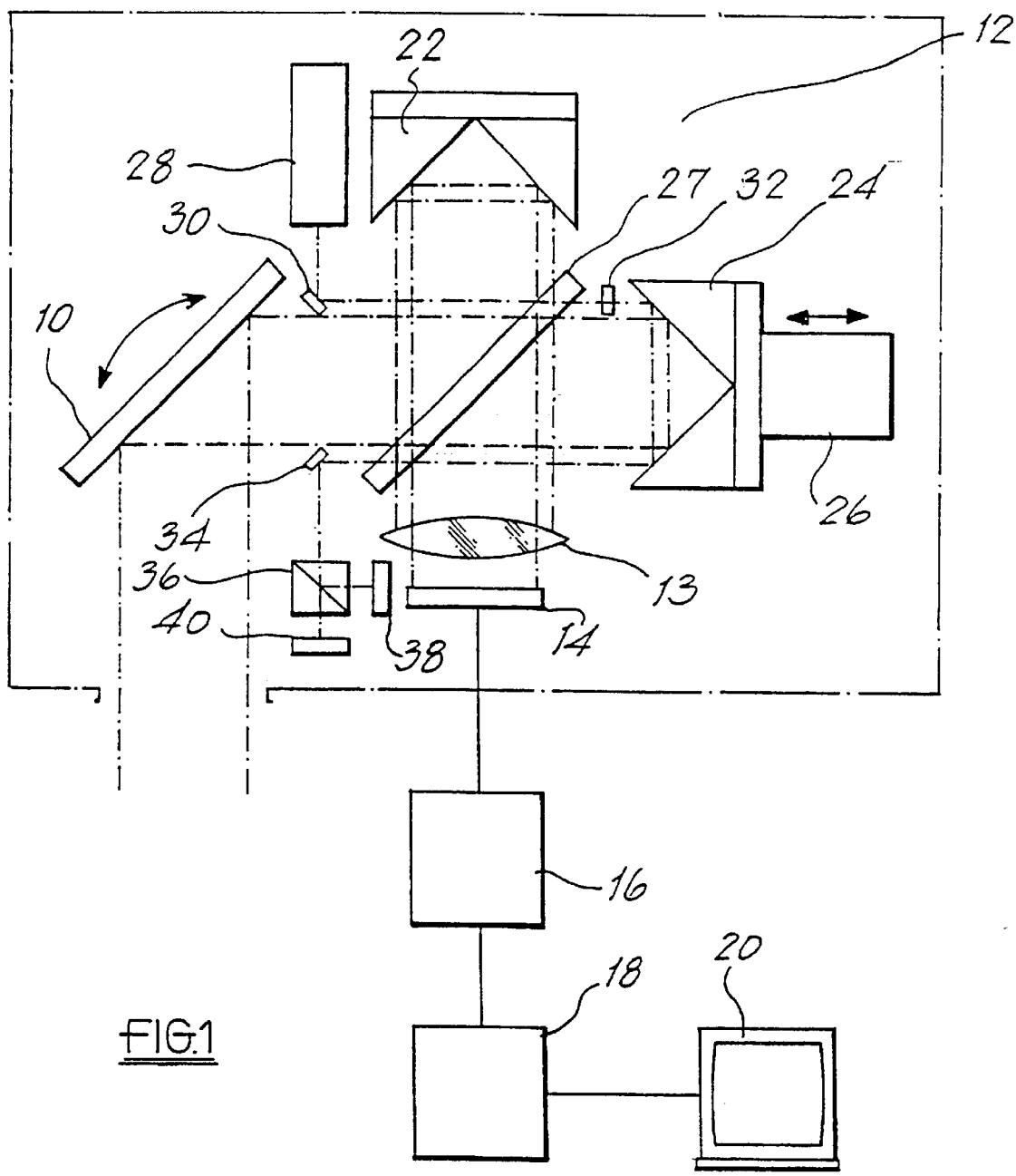
FIG. 1 is a schematic diagram of a gas cloud imaging system.

FIG. 1 is a schematic diagram of an apparatus for imaging a quantity of gas present in the atmosphere of a selected area comprising:

an IR collection device 10 capable of collecting IR radiation in the 8–14 μm spectral region;

an interferometer 12 capable of analysing the collected IR radiation in the 8–14 μm spectral region, the interferometer 12 comprising imaging means 13 for imaging, IR radiation emerging from the interferometer 12 onto an array of IR detectors 14;

computing means 16, 18 for obtaining a plurality of IR spectra by performing Fourier transformations of the interferograms resulting from each IR detector;

display means 20 for displaying in a suitable form an IR image, said IR image comprising the plurality of IR spectra, or quantities derived therefrom;

means for measuring ambient temperature (not shown);

means for measuring the temperature of the background 16, 18;

in which the difference between the two measured temperatures is used by the computing means 16, 18 to derive gas column densities from said IR spectra.

The interferometer 12 is a Michelson interferometer having a 12°×8° total field of view. The interferometer 12 is configured to operate in the 8–14 μm range at 4 cm$^{-1}$ resolution. The benefits afforded by FTIR spectroscopy with a Michelson interferometer are well documented and include the multiplex advantage—the entire spectral region is monitored for the entire observation time—and the throughput, or Jacquinot, advantage. The latter advantage is a manifestation of the inherent axial symmetry, which permits a large circular entrance aperture to be used. This is of particular relevance to imaging, since the field of view defined by the entrance aperture can be imaged onto a one or two dimensional array detector. In this way, each array pixel records an entire interferogram of a portion of the field of view.

Clearly it is desirable that the eventual IR image obtained is two dimensional in nature, i.e. a plurality of IR measurements are made in both the vertical and horizontal directions, each measurement corresponding to IR radiation collected from a different portion of the selected area. One way of obtaining such a two dimensional image is to employ a two dimensional array with a fixed position IR collection device. Such an approach is efficient in the sense that all of the interferograms necessary to derive a complete image are obtained simultaneously during the course of one traversal of the drive mirror. However, at the present time, two dimensional arrays are extremely expensive. Furthermore, full exploitation of the simultaneous measurement capability imposes exacting data acquisition and data processing constraints. These considerations have thus far militated against the use of a two dimensional array in a commercially practical device. However, two dimensional arrays are certainly within the scope of the invention, and, indeed, advances in array manufacture and data processing technologies may in the future render two dimensional arrays a more attractive option. Compared to the alternative imaging methods described below, a two dimensional array has the advantage that additional scanning input optics are not required.

In the present embodiment the array of IR detectors 14 comprises a linear 1×8 array, and the IR collection device 10 is a one dimensional scanning optical element, preferably a mirror, the scanning mirror being moveable so as to vary the portion of the selected area from which IR radiation is imaged onto the linear array 14. Thus, the linear array 14 is arranged to view a vertical strip, and the scanning mirror 10 sweeps the horizontal coordinate of this vertical stripe, thereby scanning across the selected area from which the IR image is obtained. The scanning mirror is driven by a stepper motor (not shown). In principle, any image width (within the constraints of the scanning mirror 10) could be obtained. However, an 12×8 image, with each element of the image covering an angular range of 1°, is considered to be a reasonable compromise between field of view, target resolution, linear array cost and data acquisition time. The whole 12×8 image may be acquired in ca. a second, a time scale short enough to freeze a moving gas cloud, by scanning the mirror to twelve separate positions in angular increments of 1° and acquiring data at each of these positions. Clearly, longer acquisition times may be employed if required i.e. if absorption is small. The system can be made more efficient by obtaining a separate set of measurements as the mirror is scanned back to its starting position.

It should be noted that a third way of obtaining a two dimensional IR image is to employ two scanning mirrors and a single IR detector. The mirrors scan linearly in mutually perpendicular directions: in this way the action of the scanning mirrors serves to sweep out a plurality of horizontal or vertical strips. The advantages of the approach are cost—only a single IR detector is required—and flexibility in the choice of the number of pixels producing the image. However, the time taken to produce a single IR image is increased with respect to the two IR array approaches described above, since the positions of two mirrors must be scanned in order to accumulate each IR image.

Returning to the present embodiment, output from the detector array 14 is suitably conditioned by signal conditioning and sampling means 16, described in more detail below. Conditioned data is transferred to a computer 18 comprising a digital signal processor (DSP) board plugged into an personal computer (PC). The data comprises 96 (co-added) interferograms, corresponding to the interferograms resulting from each detector element at each of the twelve scanning mirror positions. The computer 18 performs Fast Fourier Transforms of the interferograms to produce 96 IR spectra in the 8–14 μm spectral region. The display means 20—which is the PC monitor—then displays in a suitable form an IR image, this image comprising the 96 IR spectra, or quantities derived therefrom.

There are myriad possibilities for the form of this display: some of these possibilities are discussed below, although it is understood that the display is not limited in this way. The most obvious display format is some kind of 12×8 matrix, which is of course commensurate with the actual image obtained. In principle, the ninety six IR spectra themselves might be displayed within this 12×8 matrix. More useful—especially for use in the field—is a system in which the computer 18 performs a preliminary analysis of the spectra, and the results of this analysis are displayed. For example, the computer might recognise the presence of a gas from its IR spectrum, and display, as the IR image the intensities of a characteristic absorption or emission feature (which, of course, are related to the concentration of the gas). The intensities might be displayed by using hot/cold "false colour" scheme, with an on-screen indication of what gas has been detected. An alternative would be a monochrome grey scale coding of intensity. Another alternative still would be to assign a different colour to different gases, and to indicate the relative or absolute concentration of the gas by varying the shade of the assigned colour. The task of spectral analysis might be simplified by preselecting the gas or gases to be detected, so that the computer only analyses the spectra for a small number of spectral features—probably just one—at characteristic wavelengths.

It is not, of course, essential that the whole image—in this case a 12×8 image—be displayed. If desired, images of reduced dimensionality, for example 8×8, may be conveniently produced using appropriate software.

An important embodiment of the present invention is an apparatus which further comprises a camera capable of generating a visible image of an area which includes the selected area, and in which the display means 20 displays the visible image simultaneously with the display of the IR image.

Figure 3:
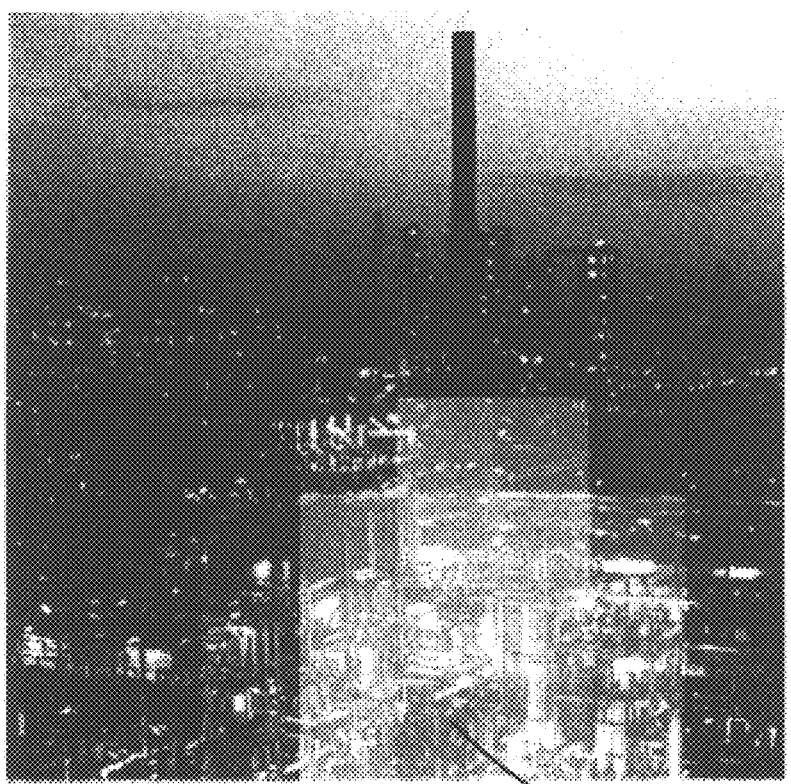
FIG. 3 is a composite display of a visible image and an 8×8 image of a slow gas leak.
Figure 2:
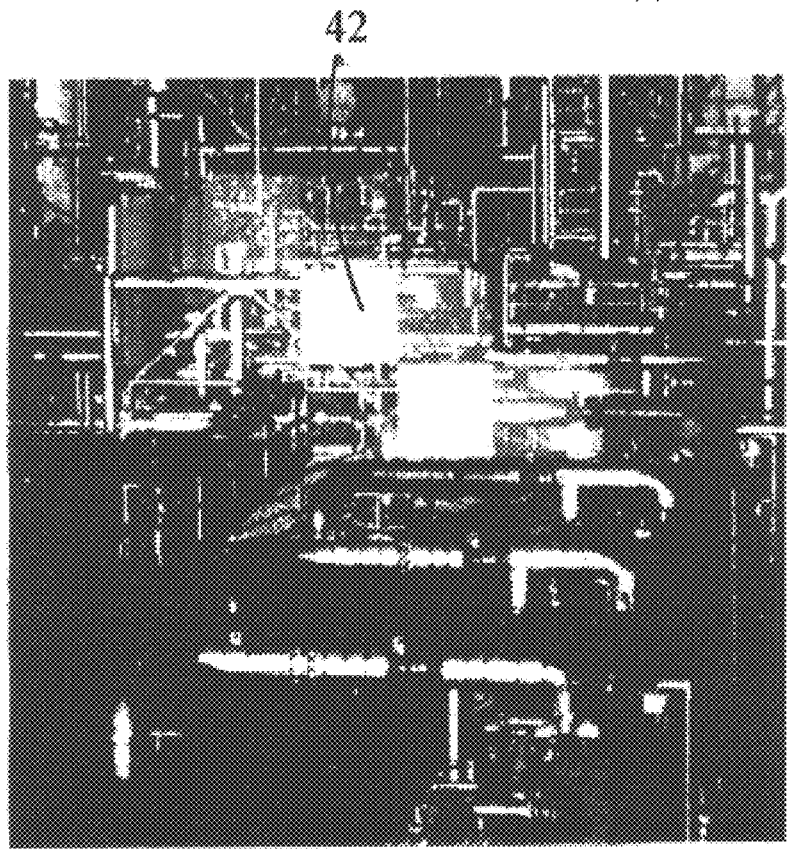
FIG. 2 is a composite display of a visible image and an 8×8 image of a fast gas leak.

This combination of display images is especially powerful if the IR image is displayed in the portion of the visible image which substantially corresponds to the selected area from which the IR image is derived. In that way, a user is given a clear indication of the exact area being imaged by the FTIR system. Simulations of the form of such a display have been performed using two realistic scenarios: a high pressure leak from a pipe, producing a clearly defined plume, and a slower, fugitive, leak producing a large, slowly spreading cloud of gas. The simulations were produced by manufacturing a high quality image of the gas plume, and then reducing the spatial resolution before superimposing the reduced resolution image—in this case a 8×8 image—onto the background scene. FIG. 2 shows an 8×8 pixel image 42 of the high pressure gas leak, whilst FIG. 3 shown an 8×8 pixel image 44 of the slower gas leak. An 8×8 image appears to be sufficient to generate an image of acceptable quality, however, the generation of images of higher resolution is certainly within the ambit of the invention. FIGS. 2 and 3 are in monochrome with gas concentration displayed with grey scale coding. Further simulations have indicated that the data may be more easily interpreted by a user if a colour visible image is displayed and a monochrome IR image is overlaid or if a monochrome visible image is displayed and a colour IR image is overlaid. There are many possible forms of image presentation. If night monitoring is required, a visible image acquired during the day may be stored for simultaneous display with the IR image.

A preferred method for generating the visible image is to locate the camera on the housing in which the scanning mirror is mounted. The camera may then be easily oriented in general alignment with the scanning mirror. A single visible frame from the camera is then acquired in the middle of a mirror scan. It is not necessary that the image be updated during every mirror scan: usually it is sufficient that the image is updated every two minutes or so, although this interval is flexible.

The camera is preferably a low cost panchromatic CCD TV camera equipped with a suitable lens (i.e. a lens having a field of view similar to or wider than that of the widest IR image). The computer 18 is equipped with a framestore card, and commercially available software may be used to drive both the camera and the image data acquisition, these processes being triggered by the master control program. No special alignment procedure should be required if the apparatus is moved from site to site: all that is required is an initial mapping of the IR onto the visible image so that the two may be accurately overlaid by the display software.

It should be noted that the principle of displaying the visible image simultaneously with the IR image can be extended to non-quantitative IR imaging, for example to non-quantitative IR imaging in the 3–5 μm spectral region.

The present invention can provide quantitative data since column densities (dimensions of concentration×length—typically expressed as ppm.meters) may be derived from the IR spectra. Quantitative data is important in the context of gas leaks and clouds because it indicates how much gas is present and whether hazardous or explosive thresholds are being exceeded.

In the limit of infinite temperature difference between IR source and absorbing gas, the absorbance (A) is given by Beer's law:

$$A = \ln\left(\frac{I_0}{I_T}\right) = kcl \quad (1)$$

where $I_o$ is the IR intensity before attenuation by the gas, $I_T$ is the intensity of the transmitted IR radiation, k is the absorption coefficient, c is the concentration and l is the absorption path length. Thus, knowledge of k—either from the literature or from prior calibration—can provide the column density cl from measured values of absorbence or transmittance. However, when the temperature difference ΔT between source and gas is small—small in the context being 30° C. or less—a wavelength dependent correction factor needs to be applied to the spectra to account for the apparent decrease in absorption on emission intensity.

This wavelength dependent correction factor is derived as follows.

Consider a column of gas of length l and concentration c in thermal equilibrium at a temperature $T_g$. The intensity of the emission from the end of the column, $I_g$, is given by the equation (2):

$$I_g = L(\upsilon, T_g)(1 - e^{-kcl}) \quad (2)$$

where $L(\upsilon,T)$ represents black body emission at a temperature $T$, $\upsilon$ is the frequency and k is the absorption coefficient. When illuminated by a background source of intensity $I_o$ at frequency $\upsilon$ and temperature $T_b$, the gas absorbs some of the energy resulting in a transmitted intensity $I_a$ given by equation (3):

$$I_a = I_o(1 - e^{-kcl}) = L(\upsilon, T_b)(1 - e^{-kcl}) \quad (3)$$

Any emission by the gas-governed by equation (2)—results in a decrease in the apparent absorption of the gas. The observed absorption is the true absorption (given by equation (3) minus the emitted intensity (given by equation (2)). A correction factor of $1/K_T$ is required to convert the observed absorption to the true absorption by the gas. $K_T$ is the ratio of the observed absorption at gas temperature $T_g$ to the true absorption, and is given by:

$$K_T = \frac{L(\upsilon, T_b)(1 - e^{-kcl}) - L(\upsilon, T_g)(1 - e^{-kcl})}{L(\upsilon, T_b)(1 - e^{-kcl})} \quad (4)$$

$$= 1 - \frac{L(\upsilon, T_g)}{L(\upsilon, T_b)}$$

but $$L(\upsilon, T) = \frac{2h\upsilon^3}{c^2} e^{-\frac{h\upsilon}{kT}},$$

where c is the speed of light, h is Planck's constant and k is the Boltzmann constant, thus $$K_T - 1 - e^{\frac{h\upsilon}{k}\left(\frac{1}{T_b} - \frac{1}{T_g}\right)} \quad (5)$$

The $1/K_T$ factor is ca. 14 for a 5° C. temperature difference for absorption or emission around 10 $\mu$m (i.e. the transmittances are ca. ¹⁄₁₄th of the transmittances measured with a large $\Delta T$). Gas clouds of the type typically monitored for industrial and environmental purposes are frequently at near ambient temperature with only a small difference between gas temperature and background temperature. It is a feature of the present invention that images can be obtained, and quantitative data can be extracted from these images, when the temperature difference is as small as 5° C. Clearly, the measurement of hotter gases is also within the scope of the invention: indeed, it is easier to extract quantitative data at higher temperature differences, where the $1/K_T$ factor approaches unity.

In the present invention the temperature of the quantity of gas and the temperature of the background are measured, and the difference between the two measured temperatures is used to derive gas column densities by way of applying temperature and wavelength dependent correction factors to the IR spectra.

It should be noted that in the foregoing derivation of the temperature dependent correction factor, a single concentration c is used to describe the gas concentration. In reality, the gas concentration in the cloud is not uniform, and therefore the derived column density will represent an average value along the line of sight.

The background temperature is derived directly from the intensity of the IR spectra, i.e. from the magnitude of the detector response(s). For obvious reasons, the intensity is measured in a part of the spectrum unmodified by the presence of gas. It has proved useful in this regard to obtain spectra of thermal emissions from a heatsink, this heatsink being part of the temperature control system on the diode laser used to provide reference fringes in the interferometer. The heatsink is maintained at a constant temperature and this provides a detector calibration in the derivation of background temperature. The scanning mirror is capable of scanning to a position where this measurement can be made. It may be possible to derive a background temperature by fitting the intensity distribution of the background spectra to the Planck equation for blackbody emission. In order to obtain a gas temperature, a measurement of ambient temperature is made, and it is assumed that with a suitable temperature sensor, such as a thermocouple, the quantity of gas is at this temperature. Another possibility is to place temperature sensors at locations closer to the source of the leak.

Returning to the present embodiment shown in FIG. 1, it is noted that apart from the scanning mirror 10 and the detector array 14, the interferometer is of generally conventional design, although the device has been specially constructed in-house in order to produce a rugged instrument capable of use in the field. All the optional components are mounted on a substantial aluminium block (not shown). The reflective optics are corner cube reflectors 22, 24 which are used in preference to plane mirrors inter alia because of their ruggedness. One corner cube reflector is mounted on a mirror drive which comprises a compact linear motor actuator 26 and a drive controller (not shown). The actuator 26 has a suspension system consisting of two co-axial counter-wound spirals. Total end-to-end displacement is at least 2.5 mm with an absolute positional accuracy of better than 0.1 $\mu$m. The corner cube reflectors 22, 24 and the beamsplitter 27 are suitably coated for optimal performance in the 8–14 $\mu$m spectral region.

Measurement of the relative displacement between the two optical paths through the interferometer is performed by counting interference fringes produced by a laser beam. The laser 28 is a diode laser producing light at ~680 nm. The red beam is directed by a beam steering optic 30 through a peripheral portion of the beamsplitter 27, this peripheral portion functioning as a ca. 50% beamsplitter at around 680 nm. (Only the central portion of the beamsplitter 27 is coated for 50% reflectivity between 8 and 14 $\mu$m). The transmitted portion of the red light passes through a quarter wave plate 32 before the split beams are recombined on the peripheral portion of the beamsplitter 27 and turned by a beam steering optic 34 onto a beamsplitter 36. Fringes are detected with photodiodes 38, 40.

The detector array 14 is a 1×8 linear array of 0.36 mm² (0.6×0.6 mm) mercury cadmium telluride IR detectors. The array is cooled to 77 K in a liquid nitrogen dewar. The imaging means 13, depicted schematically in FIG. 1, is a 25 mm diameter aspheric germanium lens doublet of effective focal length 50 mm. The lens aperture is therefore f/2. Calculations have indicated that this combination of size and f number provides an excellent compromise between considerations of cost, etendue, image quality and size. The germanium lens doublet provides adequate performance over the entire spectral range of 8–14 μm, providing a point spread function of better than 250 μm. However, characteristics of the imaging system employed are dictated by the precise detail of the interferometer, and therefore this choice of lens and material is necessarily flexible. For example, the design of the beamsplitter, or the use of cold shields would affect the preferred imaging system, which may comprise a number of lens elements.

Figure 4:
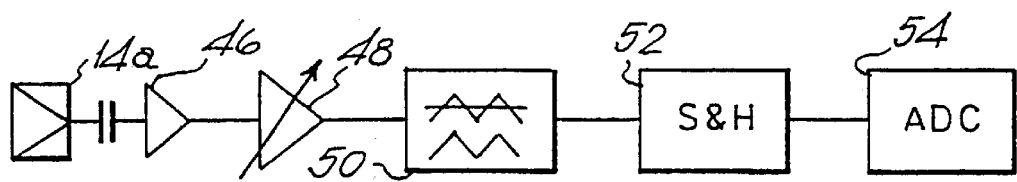
FIG. 4 is a schematic diagram of a data pre-processing system.

Interferograms resulting from each detector in the array 14 are analysed by the computer 18. As a precursor to data transfer to the computer, the outputs from the detectors are conditioned and digitised by signal conditioning and sampling means, 16. FIG. 4 is a schematic diagram of the signal conditioning and sampling performed upon the output of a single detector 14a on the array 14. The output of the detector 14a is amplified by a preamplifier 46 and variable gain amplifier 48, and frequencies above the Nyquist limit are eliminated by the low-pass anti-alias filter 50. This process should be optimised according to the characteristics of the individual detector elements in the array 14, and thus eight systems, one associated with each detector element, are required. An analogue-to-digital converter (ADC) 54 converts the analogue input into digital, suitable for data transfer by suitable means to the computer 18. The computer 18 controls the interferometer and thus a bi-directional communications link is required. Use of conventional serial or parallel interfaces is possible. In the present embodiment, direct data transfer (16 bit resolution) to the signal processing hardware is performed, via a fast synchronous serial interface (included on the DSP board plugged into the PC).

The DSP performs the necessary signal averaging, Fourier transforms, temperature corrections, and sends gas concentration data to the PC at a rate of ca. one data set (one concentration figure per pixel) per second. The PC performs numerous functions, including the archiving of data for post-processing and replay, timestamping of data, calibration procedures, self check diagnostics and hardcopy. The PC is also adapted to act as a user interface for setting up and controlling the interferometer and camera.

Figure 5:
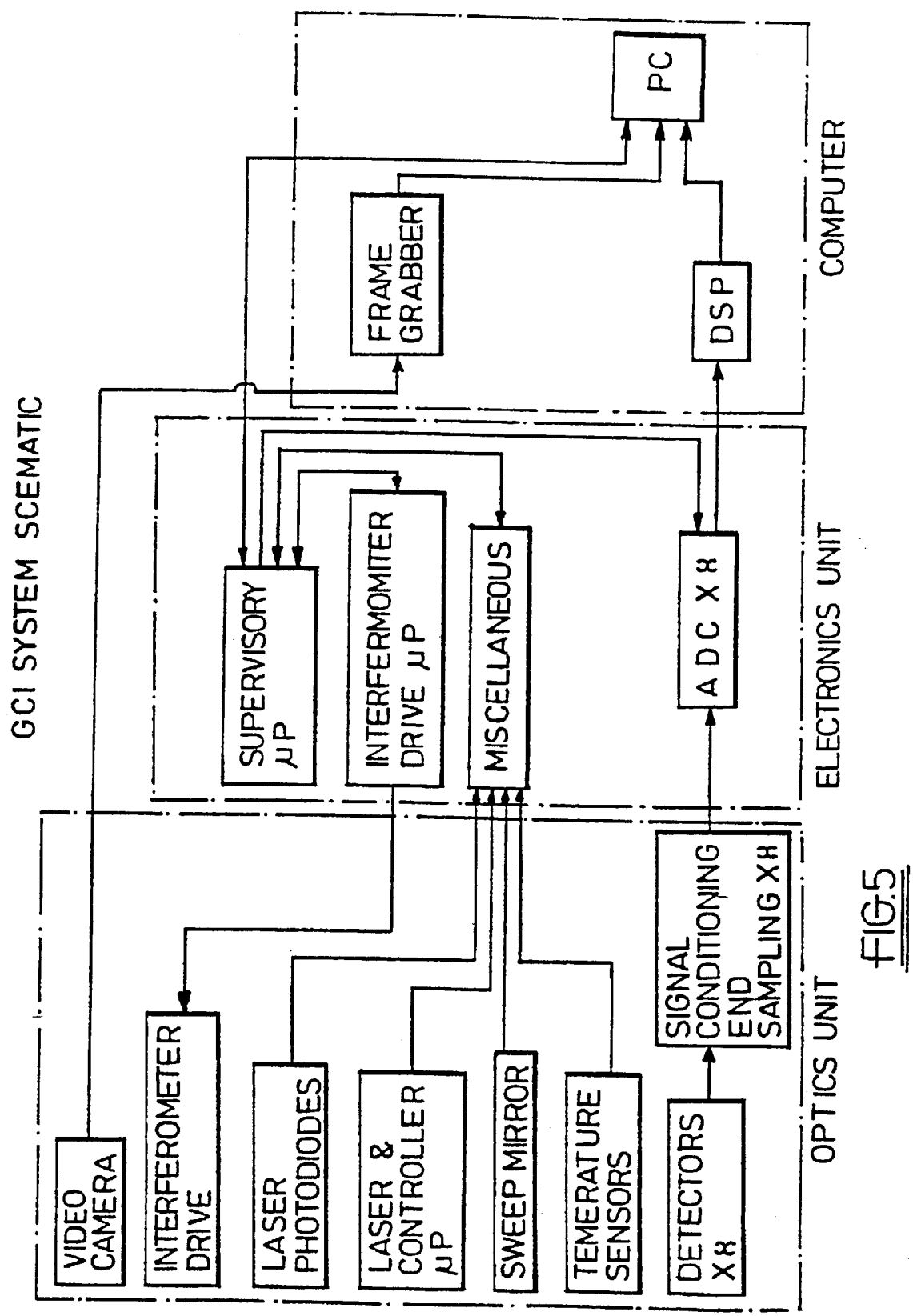
FIG. 5 is a schematic diagram of the control system.

FIG. 5 is a schematic overview of the control system. The electronics rack contains a pair of boards designed to drive specific portions of the apparatus and a "supervisory" microprocessor board, used to provide a common interface between the PC and the cards. The supervisory board also performs some instrument functions. Communication between the PC and the supervisory board is via an RS 232 link.

The interferometer mirror is driven by its own microprocessor which resides on a board in the electronics rack. Control signals for the drive are sent from the PC via the supervisory microprocessor.

The "miscellaneous" board takes the signals from the laser photoiodes, decodes these signals, controls the scanning mirror, handles the temperature sensor signal (used to measure the reference black body temperature) and provides a serial communications link to the laser module. The laser module also has its own microcontroller to drive the temperature stabilisation.

The video camera, which is mounted above the scanning mirror, feeds its signal directly to a frame grabber board in the PC, and thence to the PC software.

The invention provides a passive, quantitative IR imaging device capable of remote detection of gas clouds at ranges from meters to kilometers. Gases detectable by the invention include acetone, ammonia, aniline, benzene, toluene, xylene, butane, carbon dioxide, hydrogen sulphide, phosgene, propane, sulphur dioxide and vinyl chloride. Two operating modes are provided which involve the use of different observation times. A fast response mode having an observation time of 10 seconds is provided for rapid response to dangerously high levels of gases—for example, potentially explosive concentrations of hydrocarbons. A slower response mode having an observation time of 5 minutes is provided for detecting gases with higher sensitivity: for example, a fugitive gas leak. Other response modes are, of course, also within the scope of the invention.

There are numerous modifications to the systems which might readily occur to those skilled in the art. For example, the sensitivity of the apparatus might be improved by the incorporation of cold shields into the interferometer. Another possibility is the incorporation of a central control system which would take over some or all of the function of the PC. Another possibility still is to provide a measure of the quality of the IR data. For example, the quality of the derived gas column densities might be displayed as a confidence factor, ranging from 0% (completely unreliable data) to 100% (maxium confidence). A plurality of imaging systems might be installed at various locations on a site, all of these systems reporting back to the central control system. Another possibility still is the provision of an alarm which would be activated if the amount of gas exceed a predetermined threshold. Such an alarm might be audible and/or visual, possibly via a central monitor. Since the present invention provides information concerning the location of a gas release, the system could, for example, selectively trigger alarms in the vicinity of the gas release or effect a shutdown procedure by closing valves, etc, at the location in question.

What is claimed is:

1. A method for imaging a quantity of gas present in the atmosphere of a selected are comprising the steps of:

directing background infra-red radiation from the selected area into an interferometer;

imaging the infra-red radiation emerging from the interferometer onto at least one infra-red detector;

obtaining a plurality of Fourier transform infra-red spectra in the 8–14 μm spectral region, each spectrum corresponding to infra-red radiation collected form a different portion of the selected area;

displaying an infra-red image, said infra-red image comprising the plurality of infra-red spectra, or quantities derived therefrom; and measuring the temperature of the quantity of gas or the ambient temperature, measuring the temperature of the background and utilizing the difference between the two measured temperatures to derive gas column densities from said infra-red spectra.

2. A method according to claim 1 in which the infra-red radiation emerging from the interferometer is imaged onto an array of infra-red detectors, and each spectrum in the plurality of infra-red spectra corresponds to the transformed output of a detector in the array.

3. A method according to claim 1 in which the background temperature is measured from the intensity or the intensity distribution of the infra-red spectra.

4. A method according to claim 1, in which an infra-red image comprises quantities related to the intensity of an absorption or emission feature in the plurality of infra-red spectra.

5. A method according to claim 1, in which the difference between the two measured temperatures is less than 20° C.

6. Apparatus for imaging a quantity of gas present in the atmosphere of selected area comprising:

an infra-red collection device capable of collecting infra-red radiation in the 8–14 μm spectral region comprising imaging means for imaging infra-red radiation emerging from the interferometer onto at least one infra-red detector, the interferometer producing a plurality of interferograms, each interferogram corresponding to a different portion of the selected array;

computing means for obtaining a plurality of infra-red spectra by performing Fourier transformations of the plurality of interferograms;

display means for displaying an infra-red image, said infra-red image comprising the plurality of infra-red spectra, or quantities derived therefrom;

means for measuring the temperature of the quantity of gas or the ambient temperature;

means for measuring the temperature of the background;

in which the difference between the two measured temperatures is used by the computing means to derive gas column densities from said infra-red spectra.

7. Apparatus according to claim 6 in which the interferometer is a Michelson interferometer.

8. Apparatus according to claim 6 comprising an array of infra-red detectors in which infra-red radiation emerging from the interferometer is imaged onto said array and the computing means performs Fourier transformations on the interferograms resulting from each infra-red detector.

9. Apparatus according to claim 8 for generating a two dimensional infra-red image comprising a two dimensional array of infra-red detectors.

10. Apparatus according to claim 8 for generating a two dimensional infra-red image in which the array of infra-red detectors comprises a linear array, and the infra-red collection device is a scanning optical element, the scanning optical element being moveable so as to vary the portion of the selected area from which infra-red radiation is imaged onto the linear array.

11. Apparatus according to claim 10 in which the linear array comprises at least eight infra-red detectors.

12. Apparatus according to claim 6, in which the display means displays an infra-red image comprising quantities related to the intensity of an absorption or emission feature in the plurality of infra-red spectra.

13. Apparatus according to claim 6, in which the imaging means is an aspherical germanium lens combination.

14. Apparatus according to claim 6, in which the interferometer comprises corner cube retroreflectors.

15. Apparatus according to claim 14 in which the detectors comprise cooled mercury cadmium telluride detectors.

* * * * *

UNITED STATES PATENT AND TRADEMARK OFFICE
CERTIFICATE OF CORRECTION

PATENT NO. : 6,297,504 B1
DATED : October 2, 2001
INVENTOR(S) : Michael Paul Andreou It is certified that error appears in the above-identified patent and that said Letters Patent is hereby corrected as shown below:

Title page,
Item [57], ABSTRACT,
Line 6, "Fouriertransform" should read -- Fourier transform --.
Line 8, "coitesponding" should read -- corresponding --.

Column 1,
Line 28, after simplicity, insert -- . It --.

Column 3,
Line 17, "man" should read -- may --.
Line 46, "by," should read -- by --.

Column 4,
Line 8, "imagine" should read -- imaging --.

Column 6,
Line 20, "arc" should read -- are --.
Line 49, "stripe" should read -- strip --.

Column 7,
Line 16, "an" should read -- a --.

Column 8,
Line 7, "shown" should read -- shows --.
Line 64, "absorbence" should read -- absorbance --.

Column 9,
Line 14, "$T_h$" should read -- $T_b$ --.
Line 19, "emissionby" should read -- emission by --.

Column 11,
Line 53, "photoiodes" should read -- photodiodes --.

UNITED STATES PATENT AND TRADEMARK OFFICE
CERTIFICATE OF CORRECTION

PATENT NO. : 6,297,504 B1
DATED : October 2, 2001
INVENTOR(S) : Michael Paul Andreou It is certified that error appears in the above-identified patent and that said Letters Patent is hereby corrected as shown below:

Column 12,
Line 34, "are" should read -- area --.
Line 41, "form" should read -- from --.

Signed and Sealed this

Twenty-second Day of April, 2003

JAMES E. ROGAN
*Director of the United States Patent and Trademark Office*